United States Patent [19]

Shapiro

[11] 4,440,158

[45] Apr. 3, 1984

[54] ANKLE SUPPORTER

[76] Inventor: Martin Shapiro, Park City West Apts., Apt. 2-0, 3900 Ford Rd., Philadelphia, Pa. 19131

[21] Appl. No.: 386,248

[22] Filed: Jun. 8, 1982

[51] Int. Cl.³ .............................................. A61F 3/00
[52] U.S. Cl. ................................. 128/80 H; 128/166
[58] Field of Search .................. 128/80 H, 80 D, 166, 128/165

[56] References Cited

U.S. PATENT DOCUMENTS

| 4,237,874 | 12/1980 | Nelson | 128/80 H |
| 4,313,433 | 2/1982 | Cramer | 128/166 X |
| 4,323,058 | 4/1982 | Detty | 128/80 H |

*Primary Examiner*—John D. Yasko
*Attorney, Agent, or Firm*—Dann, Dorfman, Herrell and Skillman

[57] ABSTRACT

This invention represents an improvement over that of my prior U.S. Pat No. 3,028,861 in that whereas the ankle supported described and claimed in that patent provided general constriction and support for the ankle of the wearer experience with it has demonstrated that certain injuries are still possible when it is being worn, particularly sprain the medial and lateral malleolus protuberances of the tibia and fibula, at their articulation with the talus bone of the ankle and injury to the ligaments supporting these joints.

1 Claim, 5 Drawing Figures

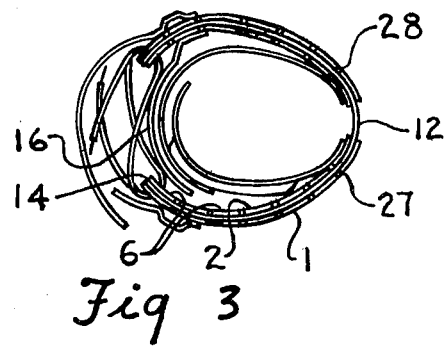
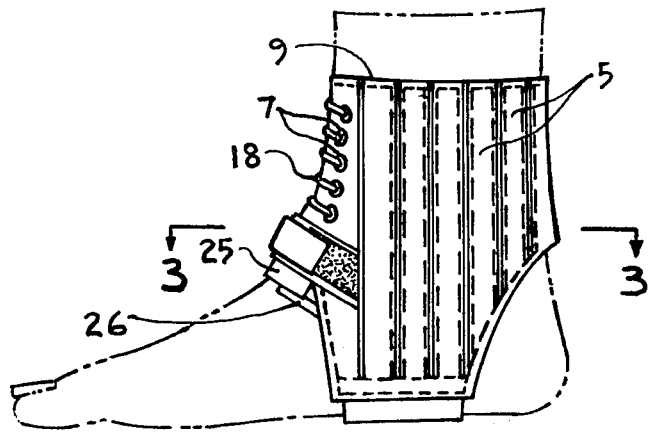
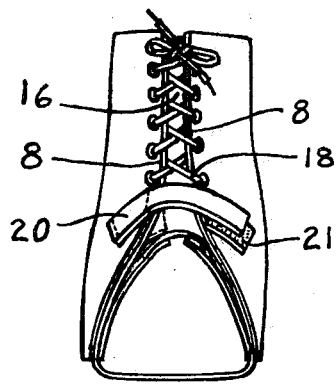
Fig 1
Fig 2
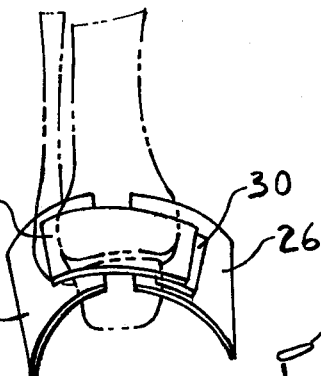
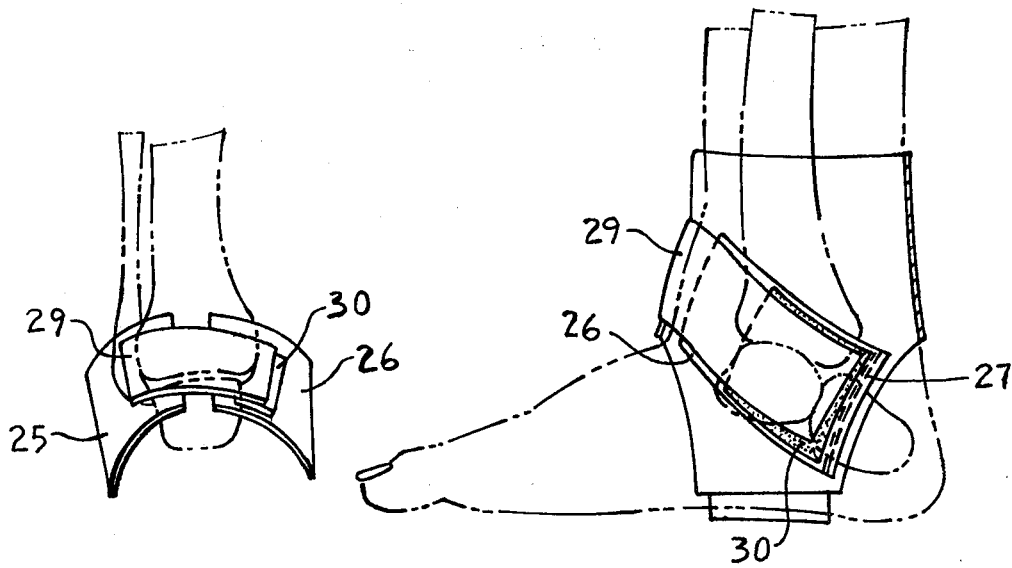
Fig 5
Fig 4

ANKLE SUPPORTER

SUMMARY OF THE INVENTION

More particularly, the invention provides, in addition to the general support afforded by the supporter of the said prior patent specifically localized supporting means for these malleolus joints as in the embodiment illustrated in the accompanying.

DRAWING in which

FIG. 1 is a front elevation of the improved ankle supporter embodying the present invention;

FIG. 2 is a side elevation of the same applied to a human foot diagrammatically illustrated to facilitate understanding of the relationship of the supporter and the foot while the supporter is being worn;

FIG. 3 is a horizontal section of the line 3—3 in FIG. 2;

FIG. 4 is a side elevation corresponding to FIG. 2 but with outer layers of the supporter broken away to show more clearly the inner malleolus-supporting structure in relation to the bone components of the ankle illustrated in broken lines;

FIG. 5 is a front elevation of the supplementary reinforcing strap structure of the present invention separated from the supporter.

DETAILED DESCRIPTION OF THE INVENTION

More particularly, in the drawing, the main ankle supporting structure comprises, as in said prior patent, an outer ply 1 and inner lining 2, both desirably made of glove leather, but in a departure from the structure of the ankle supporter disclosed in my said prior patent, in accordance with the present invention the outer ply 1 and inner ply 2 at their lower edges beside of the instep terminate in horizontal straight edges secured by stitching 3 to a section of elastic webbing 4 subtending the arch of the foot and cooperative with the malleolus supporting elements of the supporter as will hereinafter more fully appear.

As in the said prior patent the outer ply 1 and inner ply 2 are provided with a series of substantially parallel spaced slits forming a plurality of complementary elongated outer flaps 5 and inner flaps 6 on either side of the supporter lace-receiving eyelets 7 inserted in complementary spaced holes being respectively arranged in series adjacent the "front" edges 8 of the supporter.

The leather blanks from which the outer ply 1 and lining 2 are made have parallel upper straight edges which assist in forming the upper edges 9 of the supporter surrounding the the lower calf when the supporter is being worn, these edges of course being interupted by the slits which define flaps 5 and 6 as indicated in FIG. 2. Between the series of flaps and extending from one front edge of the supporter to the other, and bridging the rear edges of the flaps to expose an uncovered strip 12 overlying the tendon of achilles when the supporter is being worn there is interposed a one-piece elastic fabric insert 14 which is secured by stitching to the flaps. It affords relative independence of the flaps to conform to the contour of the ankle of the wearer while providing constrictive support to the ankle joint generally, being in this regard substantially identical in structure to corresponding component of the ankle supporter of my said prior patent.

As in said patent, furthermore, a glove leather tongue 16 is attached to the inner lining by the stitched seams adjacent the front of the supporter and positioned to underlie lace 18 when the supporter is being worn while a supplementary strap comprising relatively adjustable complementary parts 20, 21 of "Velcro" or the like, also as in said patent provides additional support for the ankle joint generally.

It has been found, however, that the ankle supporter of my prior patent does not provide adequate local support for the joints formed by the articulation of the lateral malleolus and the medial malleolus with the talus or sufficient reinforcement to the ligamenti malleoli (malleolus ligaments) which normally bind these joints together, when the wearer is engaged in activities subjecting these joints to undue stress.

To overcome this observed deficiency of the ankle supporter of my said prior patent I have devised and incorporated in the structure of the present invention a supplementary reinforcing strap or band specifically positioned to overlie the ligamentum malleoli lateralus and anterius to assist it in preventing dislocation or undue strain of said joint, said band comprising cooperative elastic straps 25,26, secured by stitching 27, 28 at the boundaries of the rear heel opening of the supporter adapted for adjustable and releasable securement by complementary "Velcro" strips 29, 30, secured thereto by appropriate stitching which enables the wearer to apply the appropriate amount of tension to reinforce the malleolus joints independently of the tension generated by adjustment of the outer strips of the lacing.

I claim:

1. An ankle supporter comprising substantially coextensive inner and outer plies of inelastic flexible material having parallel slits forming mutually registering flaps extending in the plies from the upper edges thereof substantially to portions adapted to underlie the instep of the wearer's foot, a unitary body of flexible elastic sheet material interposed between the plies and stitching securing the flaps of the inner ply respectively to the flaps of the outer ply in embracing relation to said elastic material, and stitching being inwardly spaced from the edges of the slits and the elastic material bridging the slits when in unstretched condition maintaining adjacent slit edges in mutual engagement and extending between spaced opposed rear edges of the plies, each of the latter having a series of holes adjacent its front edge for reception of lacing for holding said edges in predetermined relation, an adjustable strap comprising separable parts respectively secured to the supporter adjacent each said series of holes adapted to overlie that portion of the supporter proximate the upper front region of the wearer's instep and malleolus ligament supporting means comprising elastic straps secured to the plies extending angularly forward from said opposed rear edges and adapted to overlie said malleolus ligaments when the supporter is being worn and cooperative means carried respectively by said straps for adjustably and releasably securing to each other the free ends of the straps to apply inward pressure against said ligaments to inhibit dislocation of the malleolus joints or the wearer's ankle.

* * * * *